United States Patent [19]

Koberstein et al.

[11] Patent Number: 4,909,916

[45] Date of Patent: Mar. 20, 1990

[54] METHOD OF WORKING UP THE SOLUTION FROM THE ENZYMATIC RESOLUTION OF A RACEMATE OF AN N-ACETYL-DL-AMINO-CARBOXYLIC ACID

[75] Inventors: Edgar Koberstein, Alzenau; Thomas Lehmann, Frankfurt am Main, both of Fed. Rep. of Germany

[73] Assignee: Degussa Aktiengesellschaft, Frankfurt am Main, Fed. Rep. of Germany

[21] Appl. No.: 285,366

[22] Filed: Dec. 15, 1988

Related U.S. Application Data

[63] Continuation of Ser. No. 10,445, Feb. 3, 1987, abandoned.

[30] Foreign Application Priority Data

Feb. 8, 1986 [DE] Fed. Rep. of Germany ....... 3603986

[51] Int. Cl.$^4$ .............................................. B01D 13/02
[52] U.S. Cl. ............................... 204/182.6; 204/182.4; 204/301
[58] Field of Search ............... 204/182.6, 182.4, 182.3, 204/301

[56] References Cited

U.S. PATENT DOCUMENTS

| | | | |
|---|---|---|---|
| 2,815,320 | 12/1957 | Kollsman | 204/301 X |
| 2,835,632 | 5/1958 | Kollsman | 204/182.4 |
| 3,330,749 | 7/1967 | Kuwata et al. | 204/301 |
| 4,238,305 | 12/1980 | Ganey et al. | 204/182.4 |
| 4,238,306 | 12/1980 | Perry et al. | 204/301 X |
| 4,670,125 | 6/1987 | Mueller et al. | 204/296 |

*Primary Examiner*—John F. Niebling
*Assistant Examiner*—John S. Starsiak, Jr.
*Attorney, Agent, or Firm*—Cushman, Darby & Cushman

[57] ABSTRACT

There is described the working up of a solution by electrodialysis originally prepared by the enzymatic resolution of an N-acetyl-DL-aminocarboxylic acid. The electrodialysis device used consists of a plurality of three-chamber packets, each of which comprises a feed and diluent chamber (1), a (basic) concentrate chamber (2) located on its cathode side and an (acidic) concentrate chamber (3) located on its anode side, whereby each three-chamber packet is separated from each of the two adjacent ones by a device (4) in which water is decomposed into $OH^-$ ions and $H^+$ ions. The added resolution solution is separated by this device into three solutions, the first of which contains the L-amino acid, the second of which contains the cations present in the resolution solution as hydroxides and the third of which contains the anions present in the resolution solution as free acids.

5 Claims, 2 Drawing Sheets

METHOD OF WORKING UP THE SOLUTION FROM THE ENZYMATIC RESOLUTION OF A RACEMATE OF AN N-ACETYL-DL-AMINO-CARBOXYLIC ACID

This is a continuation of Ser. No. 010,445, filed Feb. 3, 1987, now abandoned.

BACKGROUND OF THE INVENTION

The invention is directed to a method of preparing the solution which remains after separation of the enzyme from the enzymatic resolution of racemates of an N-acetyl-DL-amino carboxylic acid in the presence of an L-amino acid acylase by electrodialysis.

When synthetically producing enantiomerically pure L-amino acids, the following indirect method is taken in many instances: The racemate which is obtained at first is acetylated and then the racemic N-acetyl-DL-amino acid is subjected to a resolution by an L-amino acid acylase. After separation of the enzyme, the L-amino acid freed by hydrolysis is isolated in a suitable manner. The nonhydrolyzed N-acetyl-D(L)-amino acid can be subjected again to a resolution of racemates after reracemization.

The solutions from the enzymatic resolution of racemates which remain after separation of the enzyme contain, for example, 0.15 to 0.7 mole/l L-amino acid, 0.15 to 0.9 mole/l N-acetyl derivates (primarily N-acetyl-D-amino acid and a lesser amount of N-acetyl-L-amino acid) and 0.15 to 0.7 mole/l acetic acid, each of the last two acids in the form of an alkali metal salt, preferably a sodium salt, and slight amounts of effector salts, e.g. of $CoCl_2$.

This solution is normally prepared by desalination by passing it over an ion exchange column filled with strongly acidic cation exchange material. Depending on the method of operation, one obtains a more or less desalinated amino acid solution, a strongly acidic fraction which contains the anions as free aids and, in addition, considerable amounts of used-up regeneration solutions which contain the exchanged cations and which must normally be removed as waste water. Additional problems occur in the case of poorly or only moderately soluble amino acids due to the fact that they can precipitate as free acids in the ion exchange column and can clog it. This is normally counteracted by elevating the temperature, which, in turn, causes disadvantages if thermally labile compounds are present.

German OS No. 29 07 450 teaches a method for preparing such solutions by electrodialysis. The known method is performed in an electrodialysis device which consists of a large number of chambers which are alternatingly separated from each other by cation and anion exchange membranes which, for their part, are positioned between a single electrode pair. Aside from the anode and the cathode cell, the chambers are operated in such a manner that one chamber funtions as feed and diluent chamber and the adjacent chamber as concentrate chamber in a constantly alternating manner. The solution to be prepared is circulated in the feed and diluent chambers and during the electrodialysis the anions and cations contained in the solution can pass through the anion exchange membrane and the cation exchange membrane into the adjacent concentrate chamber. The amphoteric amino acid is held in the feed and diluent chamber by virtue of the fact that the electrodialysis device is operated at a high current density near the limit current density. A pH barrier is built up thereby on the membranes which does not allow the amphoteric amino acid to pass through the membranes. It is possible to draw off enantiomerically pure amino acids in a good yield in the form of their aqueous solutions from the diluent chambers with the known method; however, it has the disadvantage that the anions and cations originally contained can remix and, as a consequence, only aqueous salt solutions can be drawn off from the concentrate chambers.

SUMMARY OF THE INVENTION

The method of the invention is characterized in that the electrodialysis device used consists of a plurality of three-chamber packets each of which contains a feed and diluent chamber (1), a concentrate chamber (2) on the cathode side and a concentrate chamber (3) on the anode side, whereby each three-chamber packet is separated from each of the two adjacent ones by a device (4) in which water is decomposed into $OH^-$ ions and $H^+$ ions, and that after the electrodialysis an aqueous solution of the L-amino acid having at most 50% of the originally present anions in the form of their salts is drawn off from the diluent chambers (1), an aqueous solution of the originally present cations is drawn off from the concentrate chambers (2) on the cathode side as hydroxides, and an aqueous solution of N-acetyl-D(L)-amino acid and acetic acid in the form of, the free acids is drawn off from the concentrate chambers (3) on the anode side.

The devices (4) for the decomposition of water provided in the method of the invention can consist of an additional chamber which is filled with water which contains a conductivity agent to which the membranes limiting the chambers are impervious. Suitable conductivity agents are suspended, inert conductive materials such as active carbon, carbon black or spherical metallic particles or high molecular weight acids such as polyacrylic acids or polystyrene sulfonic acids or bases, e.g. optionally substituted polyethylene imines.

As an alternative, the devices (4) for water decomposition can also consist of so-called bipolar membranes. These membranes are constructed of one cation and one anion exchange membrane which are separated from one another by a thin, neutral hydrophilic layer. This structure can consist cf a homogeneous block polymerizate or of three polymerizate foils adhered to each other. Similar arrangements are readily known to those skilled in the art; however, they are all based on the same basic concept of the decomposition of water molecules in an electric field and the supplying of the adjacent concentrate chambers (2,3) with the necessary ions.

In the electrodialysis device to be used in the method of the invention, two different concentrate chambers are associated with each feed and diluent chamber (1), so that only the originally present cations can travel into the adjacent concentrate chamber (2) located on the cathode side, which cations are completed to hydroxides by $OH^-$ ions supplied from the adjacent device (4) for water decomposition and so that only the originally present anions can travel into the adjacent concentrate chamber (3) located on the anode side, which anions are completed to the free acids by $H^+$ ions supplied from the other adjacent device (4) for the decomposition of water.

Otherwise, the electrodialysis device to be used in the method of the invention is designed in a customary manner: the three-chamber packets and the devices (4) for water decomposition which separate them are located between only one electrode pair. All individual chambers are limited by one anion and cation exchange membrane each and by a sealing frame and optionally contain a support grid. An anode chamber is provided first on the anode side of the electrodialysis device which chamber is limited by a cation exchange membrane. All following chambers are constructed in such a manner that anion exchange membranes and cation exchange membranes follow each other in a regular alternation. If so-called bipolar membranes are used as devices (4) for the decomposition of water, they are constructed in such a manner that the anion-exchanging side and the cation-exchanging side fit freely into this alternation. The cathode-side concentrate chamber (2) of the last three-chamber packet functions at the same time as cathode chamber.

The advantage of the method of the invention resides especially in the fact that after the electrodialysis is over, three differently composed aqueous solutions can be drawn off. This considerably expands the latitude for the further processing. An aqueous solution can be drawn off from the feed and diluent chambers (1) as first solution which contains practically only the L-amino acid or is at least desalinated to the extent that the pure L-amino acid can be crystallized from it with high purity after concentration. The mother liquor which remains after the separation of the L-amino acid which was crystallized out can be recycled and subjected together with fresh solution from the racemate resolution to electrodialysis again. Thus, practically no waste water that has to be removed accumulates here. An aqueous solution of the originally present cations in the form of their hydroxides can be drawn off from the cathode-side concentrate chambers (2) as a second solution. This solution can likewise be completely recycled and is used to dissolve fresh N-acetyl-DL-amino acid and to set the required pH for the enzymatic resolution. Practically no waste water which has to be removed accumulates here either. Finally, an aqueous solution of N-acetyl-D(L)-amino acid and acetic acid can be drawn off from the anode-side concentrate chambers (3) as a third solution which contains no cations except for H+ ions and can, as a consequence, be reracemized and likewise completely recycled after the acetic acid and, if necessary, the water have been distilled off according to any desired method. Circumstances permitting, this third solution can also be used alternatively to recover the D-enantiomer.

Thus, the method of the invention is clearly superior to all known methods of preparation on account of the slight amount, at the most, of accumulating waste water which must be removed, on account of its gentle operating conditions—the temperature in the electrodialysis device hardly rises over 30° C.—, on account of the great purity of the crystallized L-amino acid which can be achieved and on account of the slight, at the most, material losses. It is especially suitable for obtaining enantiomerically pure neutral and basic L-amino acids, e.g. lysine, tryptophane, histidine, phenylalanine, leucine, isoleucine, threonine, methionine, valine or arginine.

DETAILED DESCRIPTION

Figure 1:
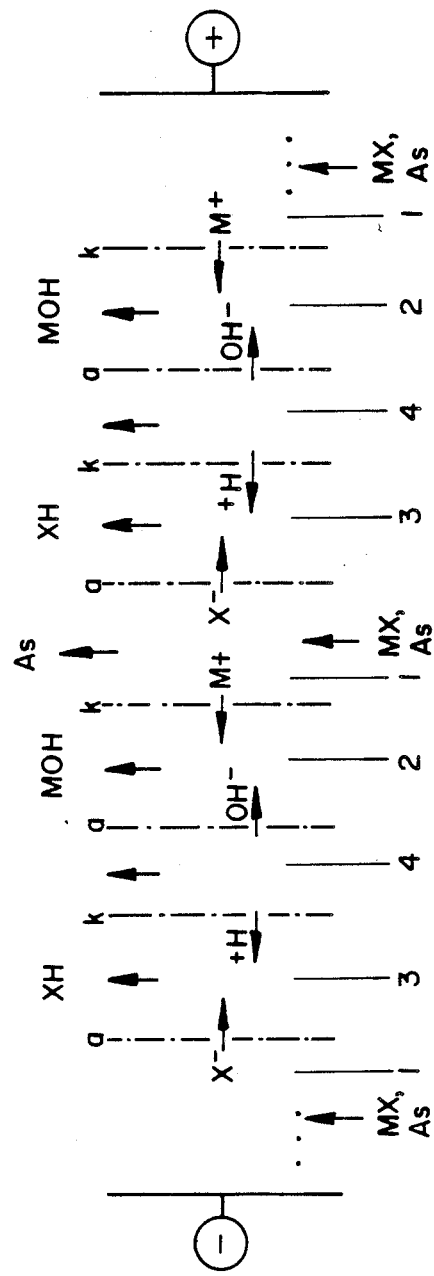
FIGS. 1 and 2 show two embodiments of the electrodialysis device to be used in the method of the invention in schematic fashion.

FIG. 1 shows an arrangement in which additional chambers are provided between the three-chamber packets as devices (4) for the decomposition of water. Reference numeral 1 designates a feed and diluent chamber, 2 a (basic) concentrate chamber located on its cathode side, 3 an (acidic) concentrate chamber located on the anode side of the feed and diluent chamber, 4 an additional chamber for the decomposition of water, k a cation exchange membrane, a an anion exchange membrane, As the amino acid, MX the salts, MOH the hydroxides produced from the M+ cations and XH the acids produced from the X− anions.

Figure 2:
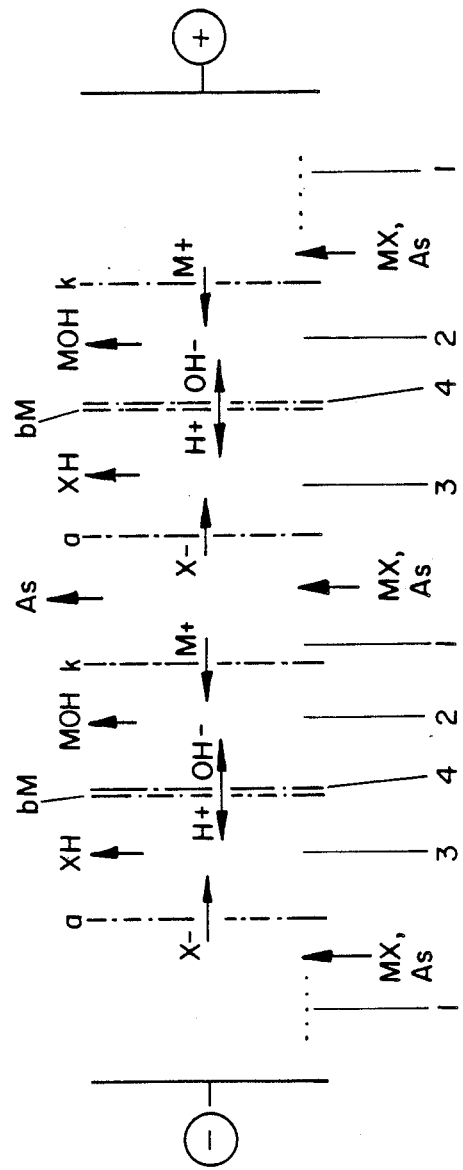

FIG. 2 shows an arrangement in which so-called bipolar membranes (bM) are provided between the three-chamber packets as devices (4) for the decomposition of water. Thus, reference numeral 4 designates a bipolar membrane while all other numerals and abbreviations have the same significance as in FIG. 1.

In order to carry out the method of the invention in a practical manner, if a device of the type shown in FIG. 1 is used, water containing the conductivity agent is filled into the additional chambers functioning as devices (4) for the decomposition of water. If a device of the type shown in FIG. 2 is used, this measure is not employed. The feed and diluent chambers (1) and the concentration chambers (2,3) are combined into three separate pump circuits, each of which contains a reservoir tank. The solution from the resolution of racemates to be prepared is pumped into the pump circuit for the diluent chambers (1), water containing a slight amount of sodium hydroxide solution for starting up the device is pumped in the pump circuit for the cathode-side concentrate chambers (2), and water containing a slight amount of acetic acid for starting up the device is pumped in the pump circuit for the anode-side concentrate chambers (3). The solutions contained in all three of the pump circuits are generally pumped with a linear flow speed between approximately 0.5 and approximately 10 cm/sec. The device is operated with direct current, the current density is a function of the particular concentration ratios and is generally located with advantage between 10 and 40 mA/cm$^2$.

The pH is advantageously maintained between 4 and 8, preferably between 5 and 7 in the pump circuit for the feed and diluent chambers (1), which can be achieved, if necessary, by the addition of acetic acid or sodium hydroxide solution. In order to preserve the anion exchange membranes it can be advantageous in the pump circuit for the cathode-side concentrate chambers (2), if the pH is limited on the upper side in such manner that it can just barely be tolerated by the anion exchange membranes. The highest admissible pH is a function of the type and properties of the anion exchange membranes used. It can be maintained by at least partially neutralizing the liquor produced by means of the addition of solid N-acetyl-DL-amino acid. In this instance, a pure liquor is not drawn off from this circuit but rather a mixture of the liquor and the corresponding salt of the N-acetyl-DL-amino acid. Since the liquid is to be used in any case to dissolve fresh N-acetyl-DL-amino acid, the mixture can also be completely recycled without any problems.

Once the desired degree of desalination has been reached in the pump circuit for the feed and diluent chambers (1), the pumps and the current are turned off.

The three circuit solutions are separately removed and processed further in the manner already described.

So much desalinated solution can be removed from the pump circuit for the feed and diluent chambers (1) in a continuous operation that the circuit is still assured. Subsequently, the volume difference is recompensated by the addition of resolution solution which has not yet been desalinated. A corresponding procedure can also be employed in the pump circuits for the concentrate chambers (2,3). It is also possible to employ a continuous "feed-and-bleed" procedure.

The invention is explained in more detail by the following examples.

The process can comprise, consist essentially of, or consist of the stated steps with the apparatus and materials recited.

EXAMPLE 1

An electrodialysis device of the type shown in FIG. 1 was used. Three independent pump circuits, each with its own reservoir tank, were set up in which the feed and diluent chambers ("diluent circuit") connected in parallel, the cathode-side concentrate chambers ("basic concentrate circuit") and the anode-side concentrate chambers ("acidic concentrate circuit") were combined.

The additional chambers, used as devices for the decomposition of water, were loaded with a 2 percent by weight suspension of a conductivity black in water and the anode chamber was filled with 1N $H_2SO_4$.

The cation exchange membranes used were based on polystyrene sulfonic acid and the anion exchange membranes used had derived pyridinium end groups.

A solution with the following composition was filled into the diluent circuit:
 32 g/l L-methionine
 92 g/l N-acetyl-D(L)-methionine as sodium salt
 38 g/l sodium acetate,
Water with a slight amount of sodium hydroxide solution was filled into the basic concentration circuit for start-up and water with a slight amount of acetic acid was filled into the acidic concentration circuit for start-up.

The three pumps were started up and set to a linear flow speed of approximately 1 cm/sec. A direct current of $i=25$ mA./cm$^2$ was applied and electrodialysis was performed until there had flowed 0.86 faraday of electricity per mole of anion initially contained in the diluent circuit.

There was now a solution with the following composition in the diluent circuit:
 41 g/l L-methionine
 36 g/l N-acetyl-D(L)-methionine as sodium salt
 2 g/l sodium acetate.

The solution had a pH of approximately 4.9 and its temperature was approximately 30° C. The volume had decreased to 78% of the initial volume.

In order to prevent a possible rise of the pH over 8, which would have damaged the anion exchange membranes, the liquor produced was repeatedly partially neutralized by the addition of solid N-acetyl-DL-methionine, so that a solution was produced with approximately 115 g/l of the sodium salt of N-acetyl-DL-methionine along with a slight amount of sodium hydroxide solution.

A solution with the following composition was present in the acidic concentrate circuit after the conclusion of the electrodialysis:
 130 g/l N-acetyl-D(L)-methionine as free acid
 38 g/l acetic acid.

The solution had a pH of 1.95. The current efficiency for the transfer of the anions was approximately 90%.

The solution from the diluent circuit was subsequently vaporized to approximately 45% of its volume. L-methionine crystallized out during cooling, and was centrifuged off and dried. The product centrifuged off was 99.7% pure, exhibited a specific rotation of $[\alpha]^{20}=24°$, had no measurable sulfate ash and contained only 0.1% N-acetyl-D(L)-methionine and 0.2% D-methionine as impurities. The crystallization mother liquor was recycled and resubjected together with fresh solution from the resolution of racemate to electrodialysis.

The solution from the basic concentrate circuit was recycled into the enzymatic resolution of racemates.

The solution from the acidic concentrate circuit was vaporized under reduced pressure almost to dryness. A solidifying melt of N-acetyl-D(L)-methionine with approximately 0.5% residual acetic acid remained. After subsequent reracemization, this product could also be recycled into the enzymatic resolution of racemates.

EXAMPLE 2

The same electrodialysis device was used as in Example 1.

The chambers used for the decomposition of water were loaded with a solution of 15 percent by weight polyacrylic acid in water. The same anion and cation exchange membranes were used as membranes limiting the chambers which were used in the rest of the membrane stack.

The desalination of the same solution as in Example 1 led under otherwise identical conditions with two diluent chambers and a total of four concentrate chambers at an average cell voltage of approximately 40 V to the same result. No loss of polyacrylic acid into the concentrate chambers could be demonstrated.

EXAMPLE 3

In the same membrane stack as in the preceding examples, the water-decomposing chamber was replaced by a bipolar membrane. The stack now contained three diluent chambers, a total of six concentrate chambers and two electrode chambers.

A solution with the following composition was filled into the diluent circuit:
 35 g/l L-valine,
 54 g/l N-acetyl-D(L)-valine as sodium salt and
 11 g/l sodium acetate.
The appropriate start solutions were filled into the concentrate circuits as in Example 1 and a 0.5 M $Na_2SO_4$ solution was filled into the electrode circuit.

After the pumps had been started, direct current with a current density of $i=25$ mA/cm$^2$ was applied to the cell, whereby an average cell voltage of 30 V developed. After the passage of an amount of electricity of 0.92 faraday per mole of anions initially contained in the diluent circuit, the desalinated solution had the following composition:
 41 g/l L-valine,
 22 g/l N-acetyl-D(L)-valine as sodium salt and
 0 g/l sodium acetate.

The solution had a pH of approximately 5, its temperature was approximately 30° C.

A solution with
 130 g/l N-acetyl-D(L)-valine as free acid and 86 g/l acetic acid could be drawn off in the acidic concentrate circuit.

The current efficiency for the transfer of anions was approximately 75%.

The solution from the diluent circuit was vaporized to approximately 40% of its volume and cooled down. L-valine with a crystallization yield of 60% was isolated by centrifuging.

The crystalline product had a content of 99%, a degree of rotation of $[\alpha]_D^{25} = 27.4°$ and an ash content of 0.01%.

The acidic concentrate solution was recirculated into the reracemization as in Example 1.

What is claimed is:

1. A process for working up the aqueous solution resulting from an enzymatic resolution of an alkali metal salt of racemic N-acetyl-DL-amino carboxylic acid in the presence of an L-amino acid acylase, said solution comprising, after separation of the enzyme, an L-amino-acid, the alkali metal salt of N-acetyl-D(L)-aminocarboxylic acid and alkali metal acetate, said process comprising the steps of (a) providing an electrodyalysis device comprising a three chamber packet, an anode and a cathode, said three chamber packet consisting of a feed and diluent chamber (1), a cathode concentrate chamber (2) and an anode concentrate chamber (3), a cathode exchange membrane separating said feed and diluent chamber (1) from said cathode concentrate chamber (2), an anode exchange membrane separating said feed and diluent chamber (1) from said anode concentrate chamber (3), means electrically connecting said cathode to said cathode concentrate chamber (2), means electrically connecting said anode to said anode concentrate chamber (3), and means for supplying $OH^-$ ions to said cathode concentrate chamber (2) and $H^+$ ions to said anode concentrate chamber, (b) supplying said aqueous solution resulting from the enzymatic resolution to said feed and diluent chamber (1), supplying an aqueous basic solution to said cathode concentrate chamber (2) supplying an aqueous acidic solution to said anode concentrate chamber (3), supplying $OH^-$ ions to said cathode concentrate chamber (2) and $H^+$ ions to said anode concentrate chamber (3), and applying direct current between said anode and said cathode through said chambers (1), (2) and (3), (c) after electrodyalysis, drawing off an aqueous solution of the L-amino acid and at most 50% of the originally present alkali metal salts of N-acetyl-DL-amino carboxylic acid from the feed and diluent chamber (1), drawing off an aqueous solution of the alkali metal cations as hydroxides from the cathode concentrate chamber (2) and drawing off an aqueous solution of N-acetyl-D(L)-amino acid and acetic acid in the form of the free acids from the anode concentrate chambers (3).

2. A method as set forth in claim 1 in which $OH^-$ ions are supplied to said cathode concentrate chamber (2) and $H^+$ ions are supplied to said anode concentrate chamber by decomposing water.

3. A method as set forth in claim 1 in which the N-acetyl-DL-amino carboxylic acid is selected from the group consisting of N-acetyl derivatives of lysine, tryptophan, histidine, phenylalanine, leucine, isoleucine, threonine, methionine, valine and aginine.

4. A method as set forth in claim 1 in which the N-acetyl-DL-amino carboxylic acid is N-acetyl-DL-methionine.

5. A method as set forth in claim 1 in which the N-acetyl-DL-amino carboxylic acid is N-acetyl-DL-valine.

* * * * *